(12) United States Patent
Elzein et al.

(10) Patent No.: US 7,271,157 B2
(45) Date of Patent: Sep. 18, 2007

(54) $A_1$ ADENOSINE RECEPTOR AGONISTS

(75) Inventors: Elfatih Elzein, Fremont, CA (US); Jeff Zablocki, Mountain View, CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 169 days.

(21) Appl. No.: 11/173,416

(22) Filed: Jun. 30, 2005

(65) Prior Publication Data

US 2006/0009417 A1 Jan. 12, 2006

Related U.S. Application Data

(60) Provisional application No. 60/587,100, filed on Jul. 12, 2004.

(51) Int. Cl.
*A01N 43/04* (2006.01)
*A61K 31/70* (2006.01)
*C07H 19/16* (2006.01)
*C07H 19/167* (2006.01)
*C07H 19/173* (2006.01)
*C07D 473/00* (2006.01)

(52) U.S. Cl. ............ 514/46; 514/263.1; 536/27.3; 536/27.6; 536/27.62; 544/264; 544/277

(58) Field of Classification Search .............. None
See application file for complete search history.

(56) References Cited

U.S. PATENT DOCUMENTS

| | | | |
|---|---|---|---|
| 6,946,449 B2 | 9/2005 | Elzein et al. | |
| 7,005,425 B2 * | 2/2006 | Belardinelli et al. | 514/46 |
| 7,144,871 B2 * | 12/2006 | Ibrahim et al. | 514/46 |
| 2003/0216349 A1 | 11/2003 | Belardinelli et al. | |
| 2004/0044225 A1 * | 3/2004 | Kanter et al. | 549/23 |
| 2005/0020532 A1 | 1/2005 | Elzein et al. | |

OTHER PUBLICATIONS

Robins, M.J. et al., "Nucleic acid related compounds. 66. Improved syntheses of 5'-chloro-5'-deoxy- and 5'-S-aryl(or alkyl)-5'-thionucleosides," Canadian Journal of Chemistry, National Research Council, Ottawa, Canada, vol. 69, No. 9, 1991, pp. 1468-1474.* van Tilburg, et al, "'N6,5'- Disubstituted Adenosine Derivatives as Partial Agonists for the Human Adenosine A3 Receptor". J. Med. Chem. Division of Medicinal Chemlstw, Leiden/Amsterdam Center for Drug Research. The Netherlands; 1999. vol. 42. pp. 1393-1400.*

Jaworski, J. S. "Nonequilibrium Solvent Polarization in Kinetics of SN2 Reactions," International Journal of Chemical Kinetics, vol. 35, No. 2, 2003, pp. 61-66.*

Van Tilburg et al, "$N^6,5'$—Disubstituted Adenosine Derivatives as Partial Agonists for the Human Adenosine $A^3$ Receptor",J. Med. Chem., Division of Medicinal Chemistry, Leiden/ Amsterdam Center for Drug Research, The Netherlands; 1999, vol. 42, pp. 1393-1400.

Robins M.J. et al., "Nucleic Acid Related Compounds. 66. Improved Syntheses of 5'-Chloro-5'-Thionucleosides", Canadian Journal of Chemistry, National Research Council, Ottawa, Canada, vol. 69, No. 9, 1991, pp. 1468-1474.

* cited by examiner

*Primary Examiner*—Cecilia Tsang
*Assistant Examiner*—Layla Bland
(74) *Attorney, Agent, or Firm*—J. Elin Hartrum; Brian Lewis

(57) ABSTRACT

Disclosed is a synthesis suitable for large scale manufacture of novel compounds that are partial and full $A_1$ adenosine receptor agonist having the structure of Formula I:

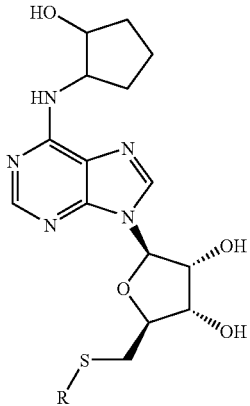

Formula I wherein R is optionally substituted phenyl, that are useful for treating various disease states, in particular tachycardia and atrial flutter, angina, and myocardial infarction.

29 Claims, No Drawings

$A_1$ ADENOSINE RECEPTOR AGONISTS

CROSS REFERENCE TO RELATED APPLICATIONS

This application claims priority to U.S. Provisional Patent Application Ser. No. 60/587,100, filed Jul. 12, 2004, the complete disclosure of which is hereby incorporated by reference.

FIELD OF THE INVENTION

The present invention relates to the preparation of compounds that are partial or full $A_1$ adenosine receptor agonists. The compounds are useful for treating mammals with diabetic disorders, obesity, modifying adipocyte function, CNS disorders, and modifying cardiac activity, in particular treatment of arrhythmia. The compounds also have antilipolytic effects in mammals.

BACKGROUND

Adenosine is a naturally occurring nucleoside, which exerts its biological effects by interacting with a family of adenosine receptors known as $A_1$, $A_{2A}$, $A_{2B}$, and $A_3$, all of which modulate important physiological processes. For example, $A_{2A}$ adenosine receptors modulate coronary vasodilation, $A_{2B}$ receptors have been implicated in mast cell activation, asthma, vasodilation, regulation of cell growth, intestinal function, and modulation of neurosecretion (See Adenosine $A_{2B}$ Receptors as Therapeutic Targets, *Drug Dev Res* 45:198; Feoktistov et al., *Trends Pharmacol Sci* 19:148-153), and $A_3$ adenosine receptors modulate cell proliferation processes.

The $A_1$ adenosine receptor mediates two distinct physiological responses. Inhibition of the cardiostimulatory effects of catecholamine is mediated via the inhibition of adenylate cyclase, whereas the direct effects to slow the heart rate (HR) and to prolong impulse propagation through the AV node are due in great part to activation of IKAdo. (B. Lerman and L. Belardinelli *Circulation*, Vol. 83 (1991), P 1499-1509 and J. C. Shryock and L. Belardinelli, *Am. J. Cardiology*, Vol. 79 (1997) P 2-10). Stimulation of the $A_1$ adenosine receptor shortens the duration and decreases the amplitude of the action potential of AV nodal cells, and hence prolongs the refractory period of the AV nodal cell. Thus, stimulation of $A_1$ receptors provides a method of treating supraventricular tachycardias, including termination of nodal re-entrant tachycardias, and control of ventricular rate during atrial fibrillation and flutter.

Accordingly, $A_1$ adenosine agonists are useful in the treatment of acute and chronic disorders of heart rhythm, especially those diseases characterized by rapid heart rate, in which the rate is driven by abnormalities in the sinoatrial, atria, and AV nodal tissues. Such disorders include, but are not limited to, atrial fibrillation, supraventricular tachycardia and atrial flutter. Exposure to $A_1$ agonists causes a reduction in the heart rate and a regularization of the abnormal rhythm, thereby improving cardiovascular function.

$A_1$ agonists, through their ability to inhibit the effects of catecholamines, decrease cellular cAMP, and thus have beneficial effects in the failing heart where increased sympathetic tone increases cellular cAMP levels. The latter condition has been shown to be associated with increased likelihood of ventricular arrhythmias and sudden death. See, for example, B. Lerman and L. Belardinelli *Circulation*, Vol. 83 (1991), P 1499-1509 and J. C. Shryock and L. Belardinelli, *Am. J. Cardiology*, Vol. 79 (1997) P 2-10.

$A_1$ agonists, as a result of their inhibitory action on cyclic AMP generation, have antilipolytic effects in adipocytes that lead to a decreased release of nonesterified fatty acids (NEFA) (E. A. van Schaick et al *J. Pharmacokinetics and Biopharmaceutics*, Vol. 25 (1997) p 673-694 and P. Strong *Clinical Science* Vol. 84 (1993) p. 663-669). Non-insulin-dependent diabetes mellitus (NIDDM) is characterized by an insulin resistance that results in hyperglycemia. Factors contributing to the observed hyperglycemia are a lack of normal glucose uptake and activation of skeletal muscle glycogen synthase (GS). Elevated levels of NEFA have been shown to inhibit insulin-stimulated glucose uptake and glycogen synthesis (D. Thiebaud et al *Metab. Clin. Exp.* Vol. 31 (1982) p 1128-1136 and G. Boden et al *J. Clin. Invest*. Vol. 93 (1994) p 2438-2446). The hypothesis of a glucose fatty acid cycle was proposed by P. J. Randle as early as 1963 (P. J. Randle et al *Lancet* (1963) p. 785-789). A tenet of this hypothesis would be that limiting the supply of fatty acids to the peripheral tissues should promote carbohydrate utilization (P. Strong et al *Clinical Science* Vol. 84 (1993) p. 663-669).

The benefit of an $A_1$ agonist in central nervous disorders has been reviewed (L. J. S. Knutsen and T. F. Murray in *Purinergic Approaches in Experimental Therapeutics*, Eds. K. A. Jacobson and M. F. Jarvis (1997) Wiley-Liss, N.Y., P 423-470). Briefly, based on experimental models of epilepsy, a mixed $A_{2A}$: $A_1$ agonist, metrifudil, has been shown to be a potent anticonvulsant against seizures induced by the inverse benzodiazepine agonist methyl 6,7-dimethoxy-4-ethyl-beta-carboline-3-carboxylate (DMCM, H. Klitgaard *Eur. J. Pharmacol.* (1993) Vol. 224 p. 221-228). In other studies using CGS 21680, an $A_{2A}$ agonist, it was concluded that the anticonvulsant activity was attributed to activation of the A1 receptor (G. Zhang et al. *Eur. J. Pharmacol.* Vol. 255 (1994) p. 239-243). Furthermore, A1 adenosine selective agonists have been shown to have anticonvulsant activity in the DMCM model (L. J. S. Knutsen In Adenosine and Adenne Nucleotides: From *Molecular Biology to Integrative Physiology*; eds. L. Belardinelli and A. Pelleg, Kluwer: Boston, 1995, pp 479-487). A second area where an A1 adenosine agonist has a benefit is in animal models of forebrain ishemia as demonstrated by Knutsen et al (*J. Med. Chem.* Vol. 42 (1999) p. 3463-3477). The benefit in neuroprotection is believed to be in part due to the inhibition of the release of excitatory amino acids (ibid).

Adenosine itself has proven effective in treating disease states related to the $A_1$ adenosine receptor, for example in terminating paroxysmal supraventricular tachycardia. However, these effects are short-lived because adenosine's half-life is less than 10 sec. Additionally, as adenosine acts indiscriminately on the $A_{2A}$, $A_{2B}$, and the $A_3$ adenosine receptor subtypes, it also provides direct effects on sympathetic tone, coronary vasodilatation, systemic vasodilatation and mast cell degranulation.

A class of compounds that are potent $A_1$ adenosine receptor agonists, full or partial, has been reported (see U.S. patent application Ser. No. 10/194,335, filed Jul. 17, 2002, the complete disclosure of which is hereby incorporated by reference). One compound disclosed in this patent application, identified as (4S,5S,2R,3R)-5-[(2-fluorophenylthio)methyl]-2-{6-[(2-hydroxy-cyclopentyl)amino]-purin-9-yl}oxolane-3,4-diol, has been shown to be a highly selective partial A1-adenosine receptor agonist.

Given the heightened interest in this and similar compounds, in particular the diastereoisomers of (4S,5S,2R,3R)-5-[(2-fluorophenylthio)methyl]-2-{6-[(2-hydroxy-cyclopentyl)amino]-purin-9-yl}oxolane-3,4-diol, it has become desirable to find a new method of synthesis that provides a convenient method for making large quantities of such compounds in good yield and high purity, avoiding the use of chromatography and other labor-intensive separation steps.

SUMMARY OF THE INVENTION

Thus, it is an object of this invention to provide a convenient synthesis for the large scale preparation of (4S,5S,2R,3R)-5-[(2-fluorophenylthio)methyl]-2-{6-[(2-hydroxy-cyclopentyl)amino]-purin-9-yl}oxolane-3,4-diol and related compounds, and its diastereoisomers, in particular 2-{6-[((1S,2S)-2-hydroxycyclopentyl)amino]purin-9-yl}(4S,5S,3R)-5-[(2-fluorophenylthio)methyl]oxolane-3,4-diol and 2-{6-[((1R,2R)-2-hydroxycyclopentyl)amino]purin-9-yl}(4S,5S,3R)-5-[(2-fluorophenylthio)methyl]-oxolane-3,4-diol.

Accordingly, in a first aspect, the invention relates to the preparation of compounds of Formula I:

Formula I

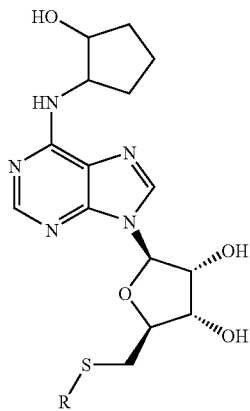

wherein R is optionally substituted phenyl, comprising the steps of:
a. in the presence of base, contacting (4S,2R,3R,5R)-2-(6-chloropurin-9-yl)-5-(hydroxymethyl)oxolane-3,4-diol with a protected (2-hydroxy) cyclopentylamine compound having a protecting group on the 2-hydroxy moiety;
b. contacting the product of step (a) with thionyl chloride in the presence of a second base;
c. contacting the product of step (b) with a third base;
d. removing the protecting group from the 2-hydroxy moiety either before or after reacting the product of step (c) with a compound of the formula RSH in the presence of a fourth base.

Accordingly, in a second aspect, the invention relates to the preparation of compounds of Formula I:

Formula I

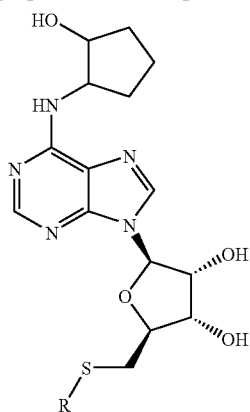

wherein R is optionally substituted phenyl, comprising contacting a compound of the formula:

(5)

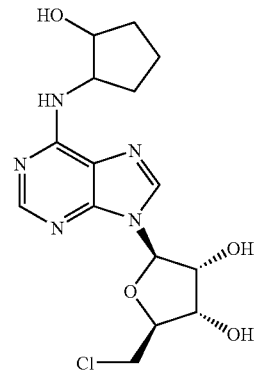

with a compound of the formula RSH in the presence of a base.

In one embodiment R is 2-fluorophenyl and the 6-substituent is (1R,2R)-2-hydroxycyclopentyl)amino. The compound of formula (5) is reacted preferably in the presence of an excess of sodium hydroxide, in a polar solvent, for example N,N-dimethylformamide.

In a third aspect, the invention relates to the preparation of a compound of the formula:

(5)

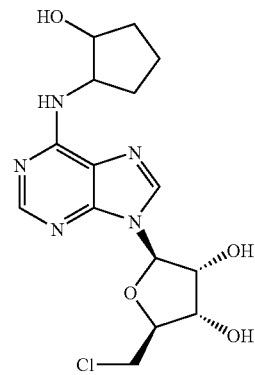

comprising contacting a compound of the formula:

(4)

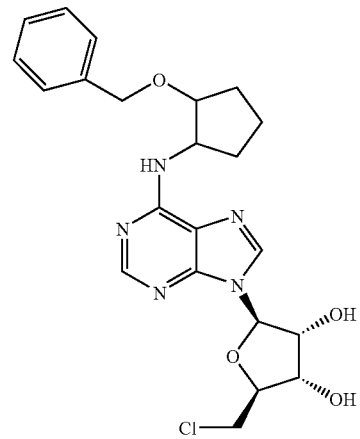

with a partially unsaturated cycloalkyl compound in the presence of a catalyst.

In one embodiment, the 6-substituent is (1R,2R)-2-hydroxycyclopentyl)amino. The partially unsaturated cycloalkyl compound is cyclohexene, and the catalyst is palladium hydroxide. The reaction is typically conducted in an inert solvent, for example ethanol.

In a fourth aspect, the invention relates to the preparation of a compound of the formula: (4)

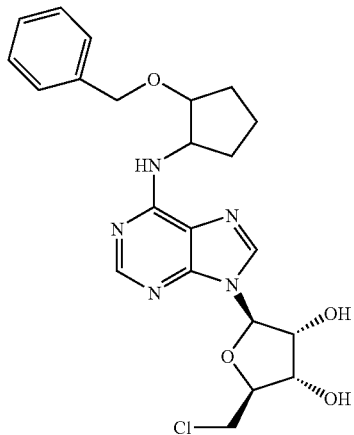

comprising contacting a compound of the formula: (3)

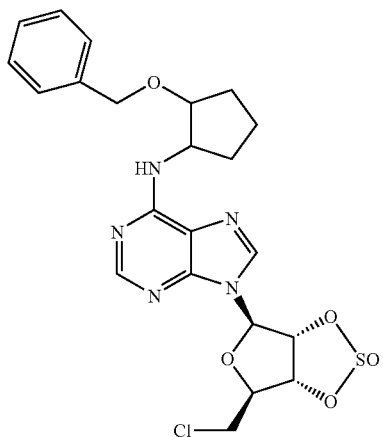

with a base.

In another embodiment, the 6-substituent is (1R,2R)-2-hydroxycyclopentyl)amino, and the bas is aqueous ammonia. The reaction may be conducted in the presence of a protic solvent, for example methanol.

In a another aspect, the invention relates to the preparation of a compound of the formula: (3)

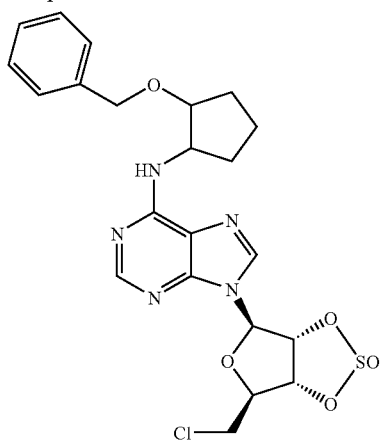

comprising contacting a compound of the formula:

(2)

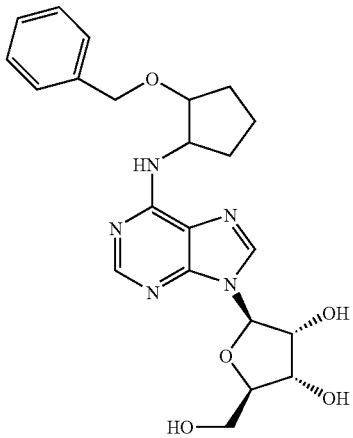

with thionyl chloride in the presence of a base.

In yet another embodiment the 6-substituent is (1R,2R)-2-hydroxycyclopentyl)amino, and the reaction is conducted in the presence of an inert solvent, for example acetonitrile. The base is typically pyridine.

In a another aspect, the invention relates to the preparation of a compound of the formula: (2)

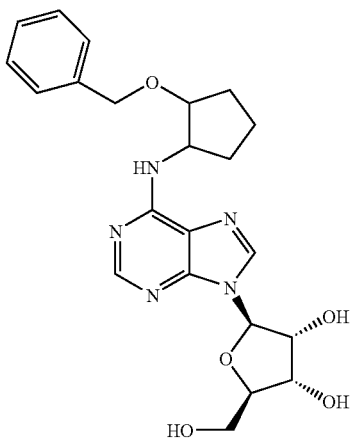

comprising contacting a compound of the formula: (1)

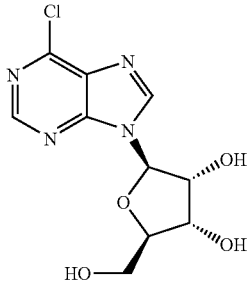

with 2-(phenylmethoxy)cyclopentylamine in the presence of a base.

In some embodiments, the reaction is conducted in the presence of an inert solvent, such as ethanol, and the base is triethylamine. The 2-(phenylmethoxy)cyclopentylamine starting material may be present as a mixture of diastereoisomers, or as individual diastereoisomers. That is, as (1S, 2S)-2-(phenylmethoxy)cyclopentylamine, (1R,2R)-2-(phenylmethoxy)cyclopentylamine, (1R,2S)-2-(phenylmethoxy)cyclopentylamine, or (1S,2R)-2-(phenylmethoxy)cyclopentylamine, or a mixture thereof. In one embodiment, the 6-substituent is (1R,2R)-2-hydroxycyclopentyl)amino.

Alternatively, the compound of formula (1) may be reacted with t-butyldimethylsilyloxycyclopentylamine in the presence of a base to prepare the t-butyldimethylsilyl protected equivalent of the compound of formula (2).

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:
1) an alkyl group as defined above, having from 1 to 5 substituents, preferably 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or
2) an alkyl group as defined above that is interrupted by 1-5 atoms or groups independently chosen from oxygen, sulfur and —NR$_a$—, where R$_a$ is chosen from hydrogen, alkyl, cycloalkyl, alkenyl, cycloalkenyl, alkynyl, aryl, heteroaryl and heterocyclyl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or
3) an alkyl group as defined above that has both from 1 to 5 substituents as defined above and is also interrupted by 1-5 atoms or groups as defined above.

The term "lower alkyl" refers to a monoradical branched or unbranched saturated hydrocarbon chain having from 1 to 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1 to 3 substituents, as defined for substituted alkyl, or a lower alkyl group as defined above that is interrupted by 1-5 atoms as defined for substituted alkyl, or a lower alkyl group as defined above that has both from 1 to 5 substituents as defined above and is also interrupted by 1-5 atoms as defined above.

The term "alkylene" refers to a diradical of a branched or unbranched saturated hydrocarbon chain, preferably having from 1 to 20 carbon atoms, preferably 1-10 carbon atoms, more preferably 1-6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "lower alkylene" refers to a diradical of a branched or unbranched saturated hydrocarbon chain, preferably having from 1 to 6 carbon atoms.

The term "substituted alkylene" refers to:
(1) an alkylene group as defined above having from 1 to 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or
(2) an alkylene group as defined above that is interrupted by 1-5 atoms or groups independently chosen from oxygen, sulfur and NR$_a$—, where R$_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or
(3) an alkylene group as defined above that has both from 1 to 5 substituents as defined above and is also interrupted by 1-20 atoms as defined above. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers(—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl: refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y-Z, in which Y is optionally substituted alkylene and Z is; optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "alkylthio" refers to the group R—S—, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1-6, preferably 1, double bond (vinyl). Preferred alkenyl groups include ethenyl or vinyl (—CH=CH$_2$), 1-propylene or allyl (—CH$_2$CH=CH$_2$), isopropylene (—C(CH$_3$)=CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1-6 sites of acetylene (triple bond) unsaturation. Preferred alkynyl groups include ethynyl, (—C≡CH), propargyl (or propynyl, —CH$_2$C≡CH), and the like. In the event that alkynyl is attached to nitrogen, the triple bond cannot be alpha to the nitrogen.

The term "substituted alkynyl" refers to an alkynyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2;

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y-Z, in which Y is optionally substituted alkylene and Z is alkenyl, cycloalkenyl, or alkynyl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl may be optionally substituted as defined herein.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and bicyclo[2.2.1]heptane, or cyclic alkyl groups to which is fused an aryl group, for example indan, and the like.

The term "substituted cycloalkyl" refers to cycloalkyl groups having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, or optionally substituted heteroaryl.

The term "heteroaryl" refers to an aromatic group (i.e., unsaturated) comprising 1 to 15 carbon atoms and 1 to 4 heteroatoms selected from oxygen, nitrogen and sulfur within at least one ring.

Unless otherwise constrained by the definition for the heteroaryl substituent, such heteroaryl groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2. Such heteroaryl groups can have a single ring (e.g., pyridyl or furyl) or multiple condensed rings (e.g., indolizinyl, benzothiazole, or benzothienyl). Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2. Heterocyclic groups can have a single ring or multiple condensed rings. Preferred heterocyclics include tetrahydrofuranyl, morpholino, piperidinyl, and the like.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—. The term "thiocarbonyl" refers to a group —C(S)—.

The term "carboxy" refers to a group —C(O)—OH.

"Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed, and the pharmaceutically acceptable salts, pharmaceutically acceptable esters, and prodrugs of such compounds. Additionally, the compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R—S system. When the compound is a pure enantiomer the stereochemistry at each chiral carbon may be specified by either R or S. Resolved compounds whose absolute configuration is unknown are designated (+) or (−) depending on the direction (dextro- or laevorotary) which they rotate the plane of polarized light at the wavelength of the sodium D line.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:
 (i) preventing the disease, that is, causing the clinical symptoms of the disease not to develop;
 (ii) inhibiting the disease, that is, arresting the development of clinical symptoms; and/or
 (iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A compound that is an agonist with high intrinsic efficacy evokes the maximal effect of which the biological system is capable. These compounds are known as "full agonists". They are able to elicit the maximum possible effect without occupying all the receptors, if the efficiency of coupling to the effector process is high. In contrast, "partial agonists" evoke a response but cannot evoke the maximal response of which the biological system is capable. They may have reasonable affinity but low intrinsic efficacy. Partial $A_1$ adenosine agonists may have an added benefit for chronic therapy because they will be less likely to induce desensitization of the $A_1$ receptor (R. B. Clark, B. J. Knoll, R. Barber TiPS, Vol. 20 (1999) p. 279-286), and less likely to cause side effects.

Nomenclature

The naming and numbering of the compounds of the invention is illustrated with a representative compound of Formula I in which R is 2-fluorophenyl:

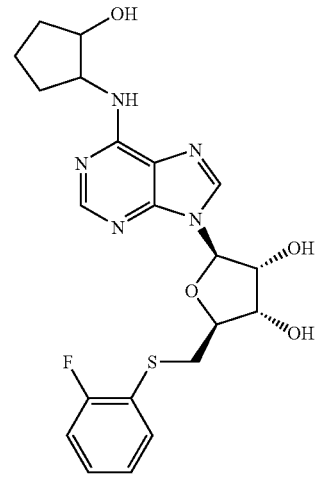

which is named:
(4S,5S,2R,3R)-5-[(2-fluorophenylthio)methyl]-2-{6-[(2-hydroxycyclopentyl)amino]-purin-9-yl}oxolane-3,4-diol,
or:
2-{6-[((1RS,2RS)-2-hydroxycyclopentyl)amino]purin-9-yl}(4S,5S,3R)-5-[(2-fluorophenylthio)methyl]oxolane-3,4-diol.

The related compound in which the 6-amino substituent is derived from (1S,2S)-2-aminocyclopentan-1-ol is named 2-{6-[((1S,2S)-2-hydroxycyclopentyl)amino]purin-9-yl} (4S,5S,3R)-5-[(2-fluorophenylthio)methyl]oxolane-3,4-diol. The related compound in which the 6-amino substituent is derived from (1R,2R)-2-aminocyclopentan-1-ol is named 2-{6-[((1R,2R)-2-hydroxycyclopentyl)amino]purin-9-yl} (4S,5S,3R)-5-[(2-fluorophenylthio)methyl]-oxolane-3,4-diol. The related compound in which the 6-amino substituent is derived from (1R,2S)-2-aminocyclopentan-1-ol is named 2-{6-[((1R,2S)-2-hydroxycyclopentyl)amino]purin-9-yl} (4S,5S,3R)-5-[(2-fluorophenylthio)methyl]-oxolane-3,4-diol. The related compound in which the 6-amino substituent is derived from (1S,2R)-2-aminocyclopentan-1-ol is named 2-{6-[((1S,2R)-2-hydroxycyclopentyl)amino]purin-9-yl} (4S,5S,3R)-5-[(2-fluorophenylthio)methyl]-oxolane-3,4-diol.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Synthesis of the Compounds of Formula I

The compounds of Formula I may be prepared starting from 6-chloropurine riboside, as shown in Reaction Scheme I:

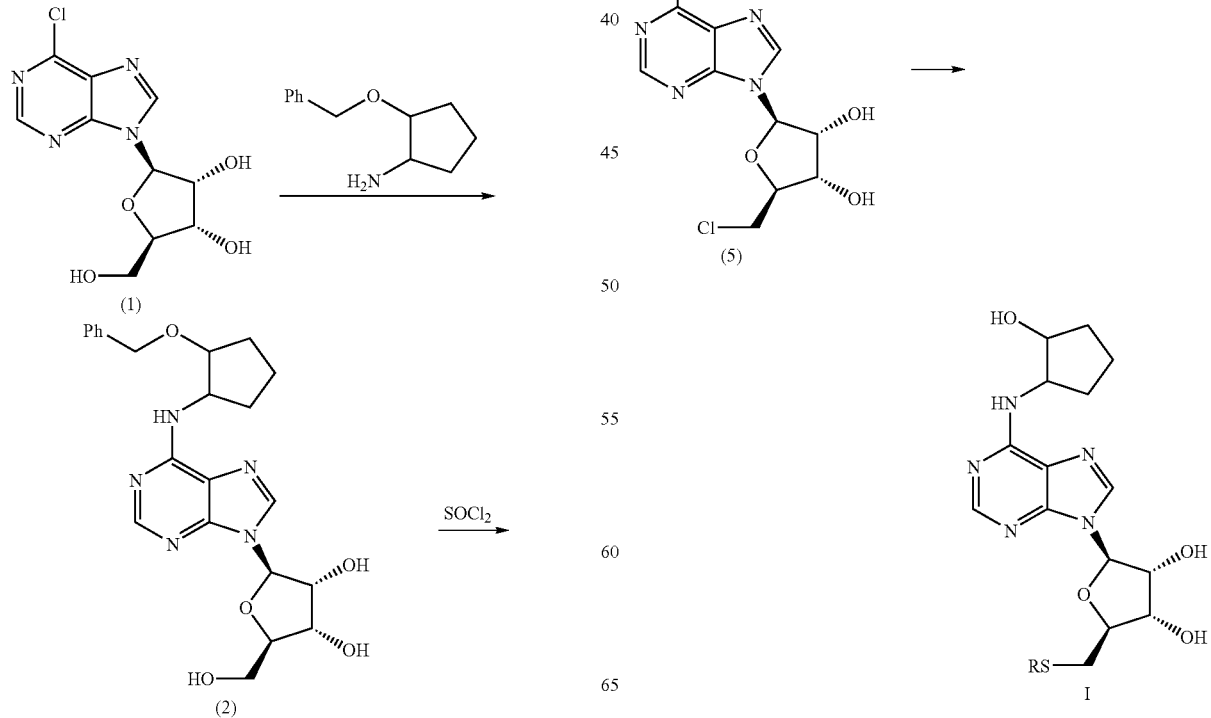

where Ph is phenyl.

Step 1—Preparation of Formula (2)

The compound of formula (2) is prepared from the compound of formula (1) by reaction with 2-(benzyloxy) cyclopentylamine in a protic solvent, such as ethanol, in the presence of a base, such as triethylamine, at a temperature of about reflux for about 24 hours. When the reaction is substantially complete, the product of formula (2) is isolated by conventional means, for example removal of the solvent under reduced pressure, partitioning the residue between ethyl acetate and water, removing the solvent from the organic layer, and purifying the residue by, for example, crystallization or precipitation from ethyl acetate/hexane.

Step 2—Preparation of Formula (3)

The compound of formula (2) is then converted to a compound of formula (3). To a suspension of the compound of formula (2) in an inert solvent, e.g., acetonitrile, is added thionyl chloride, in the presence of a base, preferably pyridine. The reaction is preferably conducted at about 0° C. for about 4 hours, and then allowed to warm to room temperature overnight. When the reaction is substantially complete, the resulting suspension is concentrated under reduced pressure to afford the compound of formula (3), which is taken to the next step without purification.

Step 3—Preparation of Formula (4)

The compound of formula (4) is prepared from the compound of formula (3) by dissolving (3) in a mixture of a base, e.g., ammonium hydroxide, and a protic solvent, e.g., methanol. The reaction is carried out at about room temperature, for about 30 minutes. When the reaction is substantially complete, the product of formula (4) is isolated by conventional means, for example by removal of the solvent under reduced pressure, partitioning the residue between ethyl acetate and water and removing ethyl acetate under reduced pressure. The residue is used in the next step with no further purification.

Step 4—Preparation of Formula (5)

The compound of formula (4) is then deprotected by treatment with a partially unsaturated cycloalkyl compound, such as cyclohexene, in the presence of a catalyst, such as palladium hydroxide. Alternatively, ammonium formate can be used in place of the unstaurate cycloalkyl compound. The reaction is conducted in a protic solvent, e.g., ethanol, preferably at about reflux, for about 18 hours. When the reaction is substantially complete, the product of formula (5) is isolated by conventional means, for example by removal of the solvent under reduced pressure, followed by trituration of the residue.

Step 5—Preparation of Formula I

The compound of formula (5) is then reacted with a compound of formula RSH, preferably 2-fluorothiophenol. The reaction is conducted in a polar solvent, preferably N,N-dimethylformamide, in the presence of a base, e.g., sodium hydroxide, at a temperature of about 100° C. for about 3-5 hours. When the reaction is substantially complete, the product of Formula I is isolated by conventional means, for example by removal of the solvent under reduced pressure, and triturating the residue with diethyl ether.

Preparation of Starting Materials 1,2-(Benzyloxy)-cyclopentylamine is used as a starting material in step 1. This compound, as the racemic mixture or as the individual isomers, is either commercially available or can be made by methods well known to those skilled in the art. For example, one method of making (1R,2R)-2-(benzyloxy)-cyclopentylamine is shown in Reaction Scheme II below.

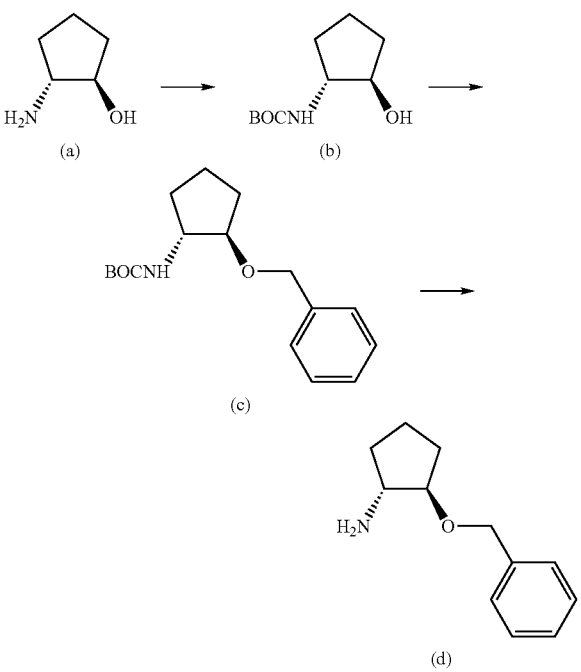

REACTION SCHEME II

In the first step, the compound of formula (a) ((1R,2R)-2-aminocyclopentan-1-ol) is N-protected with $(BOC)_2O$ (di-t-butyl dicarbonate) by conventional means, for example by reaction in an inert solvent in the presence of 4-dimethylaminopyridine. The protected cyclopentanol (b) derivative is then reacted with benzyl bromide in the presence of a base, preferably sodium hydride, to form (c), which is then deprotected in a conventional manner, with hydrochloric acid in dioxane, for example.

Starting with (1S,2S)-2-aminocyclopentan-1-ol provides a compound with the opposite stereochemistry to formula (d), and starting with (1RS,2RS)-2-aminocyclopentan-1-ol provides a racemic analog of the compound of formula (d).

It will be appreciated by those of skill in the art that the addition of the R moiety to the core structure may be carried out either before or after the removal of the protecting group from the 2-hydroxy group on the 6N cyclopentyl group. An alternative process for the preparation of compounds of Formula I utilizing a different protecting group and reversing the addition of T moiety and deprotection of the 2-hydroxy group is shown in Reaction Scheme III.

REACTION SCHEME III

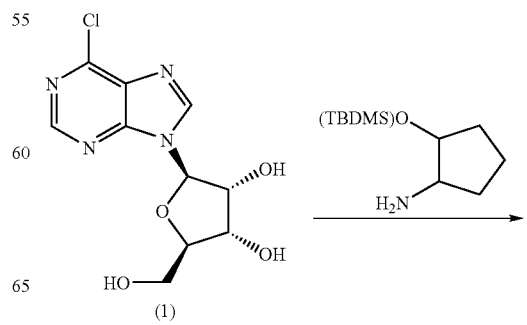

-continued

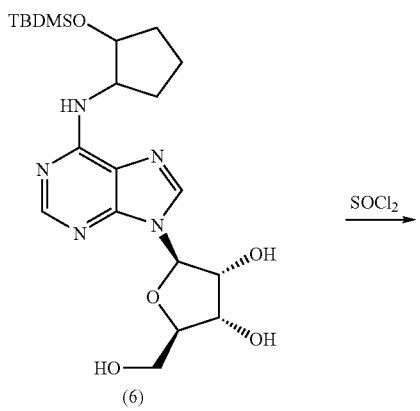

(6)

SOCl₂ →

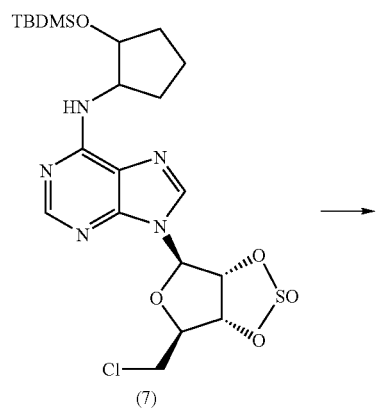

(7)

→

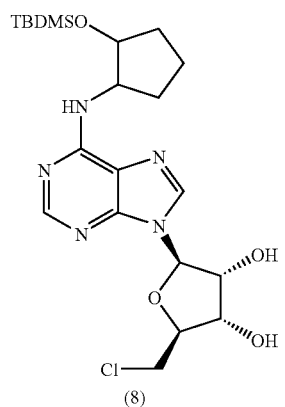

(8)

→

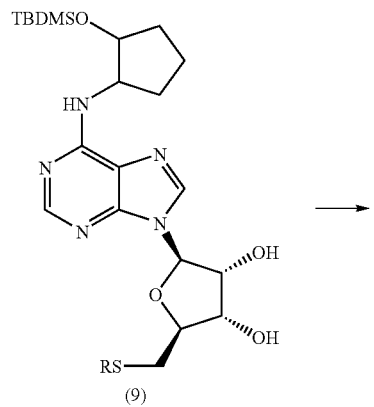

(9)

-continued

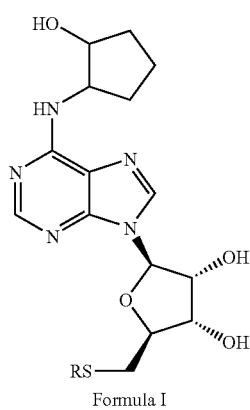

Formula I

The starting protected cyclopentyl derivative can be derived from (1R,2R)-2-aminocyclopentan-1-ol, (1S,2S)-2-aminocyclopentan-1-ol, or (1RS,2RS)-2-aminocyclopentan-1-ol. The hydroxy group is protected as a t-butyldimethylsilyl group by methods well known in the art, for example, by reaction with NH₄F in methanol.

Alternatively, the compounds of Formula I can be conveniently synthesized without using any protecting groups, as shown in Reaction Scheme IV.

REACTION SCHEME IV

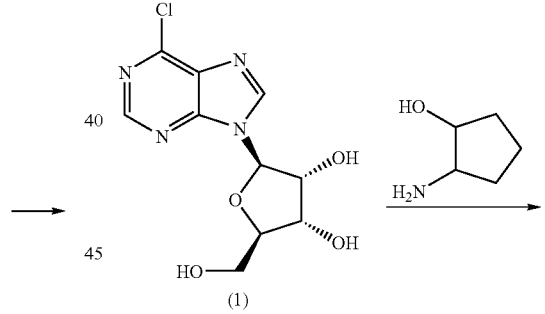

(1)

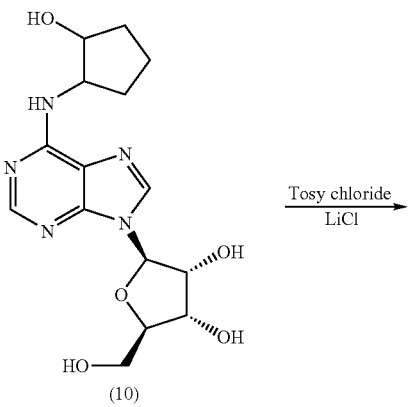

(10)

Tosyl chloride / LiCl →

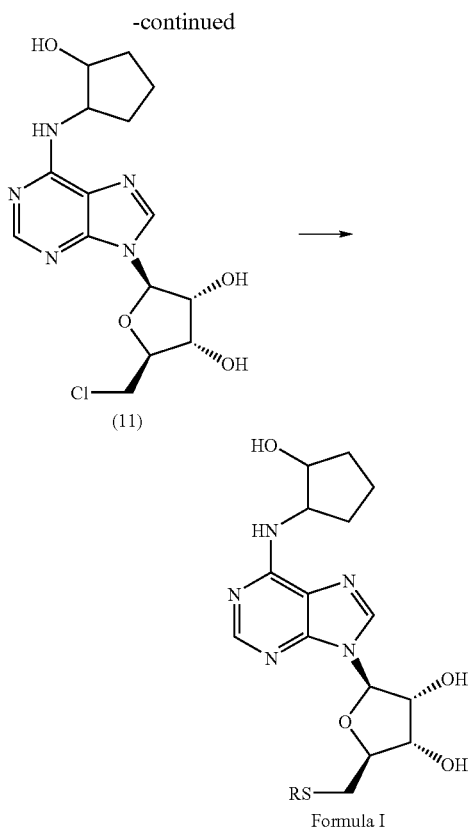

Formula I

Utility, Testing and Administration

General Utility

The compounds of Formula I are effective in the treatment of conditions that respond to administration of $A_1$ adenosine receptor antagonists. Such conditions include, but are not limited to, disease states for which diuretic treatment is appropriate, renal failure, renal dysfunction, nephritis, hypertension, oedema, Alzheimers disease, stress, depression, cardiac arrhythmia, restoration of cardiac function, congestive heart failure, diabetes, asthma, respiratory disorders, ischaemia-induced injury of the brain, heart and kidney, and diarrhea.

The compounds of Formula I are also effective in the treatment of conditions that respond to administration of $A_{2B}$ adenosine receptor antagonists. Such conditions include, but are not limited to, diarrhea, atherosclerosis, restenosis, diabetic retinopathy, Type II diabetes, cancer, senile dementia, Alzheimer's disease, Parkinson's disease, traumatic brain injury, and Type I hypersensitivity reactions, including asthma, atopic eczema, and hay fever.

Testing

Activity testing is conducted as described in those patents and patent applications referenced above, and in the Examples below, and by methods apparent to one skilled in the art.

Pharmaceutical Compositions

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. $17^{th}$ Ed. (1985) and "Modern Pharmaceutics", Marcel Dekker, Inc. $3^{rd}$ Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, it can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formula I are effective over a wide dosage range and is generally administered in a pharmaceutically effective amount. Preferably, for oral administration, each dosage unit contains from 10 mg to 2 g of a compound of Formula I, more preferably from 10 to 700 mg, and for parenteral administration, preferably from 10 to 700 mg of a compound of Formula I, more preferably about 50-200 mg. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous, or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

The following examples are included to demonstrate certain embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of a Compound of Formula (2)

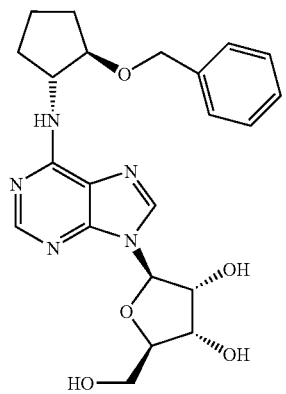

To a solution of 6-chloropurine riboside (10.0 g, 35 mmol) in ethanol (350 mL) was added triethylamine (10.0 mL, 100 mmol) and (1R,2R)-2-(benzyloxy)-cyclopentylamine (5.2 g, 52 mmol). The mixture was refluxed for 24 hours, during which the reaction went from a suspension to a clear solution. The ethanol was removed under reduced pressure, and the residue was partitioned between ethyl acetate and water (100 mL:200 mL). The organic layer was separated and the aqueous layer washed with ethyl acetate (2×75 mL). The combined organic layers were dried (sodium sulfate), and the solvent was removed under reduced pressure. The residue was dissolved in ethyl acetate (150 mL), and product precipitated by addition of hexane, to afford 2-(6-{[(1R,2R)-2-(phenylmethoxy)cyclopentyl]amino}purin-9-yl)(4S,3R,5R)-5-(hydroxymethyl)oxolane-3,4-diol as a white solid, (12.0 grams, 77%).

$^1$H NMR (CD$_3$OD) δ 1.62-2.16 (m, 6 H), 3.26-3.29 (m, 1H, NHCH), 3.68-3.85 (m, 2H, CH$_2$-5'), 4.03-4.10 (m, 1H, CH-4'), 4.12-4.16 (m, 1H, CHOBn), 4.16-4.19 (m, 1H, 3'CH), 4.71 (s, 2H, OCH$_2$Ph), 4.83-4.92 (m, 1H, 2'CH), 5.98 (d, J=6 Hz, 1H, H-1'), 7.23-7.35 (m, 5H, PhH), 8.15 (S, 1H, C-2H).

B. Preparation of a Compound of Formula (2)

Similarly, following the procedure of 1A above, but replacing (1R,2R)-2-(benzyloxy)cyclopentylamine by other isomers of 2-(benzyloxy)cyclopentylamine, the following compounds are prepared:

2-(6-{[(1S,2S)-2-(phenylmethoxy)cyclopentyl]
  amino}purin-9-yl)(4S,3R,5R)-5-(hydroxymethyl)ox-
  olane-3,4-diol;
2-(6-{[(1R,2S)-2-(phenylmethoxy)cyclopentyl]
  amino}purin-9-yl)(4S,3R,5R)-5-(hydroxymethyl)ox-
  olane-3,4-diol;
2-(6-{[(1S,2R)-2-(phenylmethoxy)cyclopentyl]
  amino}purin-9-yl)(4S,3R,5R)-5-(hydroxymethyl)ox-
  olane-3,4-diol; and
2-(6-{[(1RS,2RS)-2-(phenylmethoxy)cyclopentyl]
  amino}purin-9-yl)(4S,3R,5R)-5-(hydroxymethyl)ox-
  olane-3,4-diol.

EXAMPLE 2

Preparation of a Compound of Formula (3)

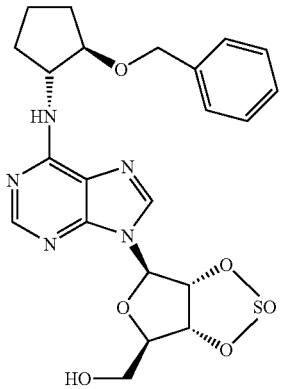

To a stirred suspension of 2-(6-{[(1R,2R)-2-(phenylmethoxy)cyclopentyl]-amino}purin-9-yl)(4S,3R,5R)-5-(hydroxymethyl)oxolane-3,4-diol (2.0 g, 4.5 mmol) in acetonitrile (15 mL) and pyridine (0.728 mL, 9 mmol) at 0 C was added dropwise thionyl chloride (1.7 mL, 22.5 mmol). After stirring for 4 hours at 0 C, the reaction was allowed to warm to room temperature, and then stirred overnight. Solvent was removed from the resulting suspension under reduced pressure, to afford 4-(6-{[(1R,2R)-2-(phenylmethoxy)cyclopentyl]amino}purin-9-yl)(6S,3aR,6aR)-6-(chloromethyl)-4H, 6H,3aH,6aH-oxolano[3,4-d]1,3,2-dioxathiolan-2-one, which was taken to the next step without further purification.

B. Preparation of a Compound of Formula (3)

Similarly, following the procedure of 2A above, but replacing 2-(6-{[(1R,2R)-2-(phenylmethoxy)cyclopentyl]-amino}purin-9-yl)(4S,3R,5R)-5-(hydroxymethyl)oxolane-3,4-diol by other isomers of 2-(6-{[2-(phenylmethoxy)cyclopentyl]-amino}purin-9-yl)(4S,3R,5R)-5-(hydroxymethyl)oxolane-3,4-diol, the following compounds are prepared:

4-(6-{[(1S,2S)-2-(phenylmethoxy)cyclopentyl]
  amino}purin-9-yl)(6S,3aR,6aR)-6-(chloromethyl)-4H,
  6H,3aH,6aH-oxolano[3,4-d]1,3,2-dioxathiolan-2-one;
4-(6-{[(1R,2S)-2-(phenylmethoxy)cyclopentyl]
  amino}purin-9-yl)(6S,3aR,6aR)-6-(chloromethyl)-4H,
  6H,3aH,6aH-oxolano[3,4-d]1,3,2-dioxathiolan-2-one;
4-(6-{[(1S,2R)-2-(phenylmethoxy)cyclopentyl]
  amino}purin-9-yl)(6S,3aR,6aR)-6-(chloromethyl)-4H,
  6H,3aH,6aH-oxolano[3,4-d]1,3,2-dioxathiolan-2-one;
  and
4-(6-{[(1RS,2RS)-2-(phenylmethoxy)cyclopentyl]
  amino}purin-9-yl)(6S,3aR,6aR)-6-(chloromethyl)-4H,
  6H,3aH,6aH-oxolano[3,4-d]1,3,2-dioxathiolan-2-one.

EXAMPLE 3

Preparation of a Compound of Formula (4)

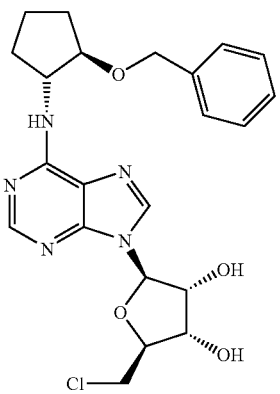

The 4-(6-{[(1R,2R)-2-(phenylmethoxy)cyclopentyl]amino}purin-9-yl)(6S,3aR,6aR)-6-(chloromethyl)-4H,6H,3aH,6aH-oxolano[3,4-d]1,3,2-dioxathiolan-2-one from Example 2 was dissolved in a mixture of methanol and water (40 mL/2 mL), and to this solution was added concentrated ammonium hydroxide (2.2 mL, 28%) dropwise. After stirring for 30 minutes at 23 C, the solvent was removed under reduced pressure and the residue diluted with water (15 mL). The aqueous mixture was extracted with ethyl acetate (3×75 mL), dried over MgSO4, and solvent removed under reduced pressure to provide 2-(6-{[(1R,2R)-2-(phenylmethoxy)cyclopentyl]amino}purin-9-yl)(4S,5S,3R)-5-(chloromethyl)oxolane-3,4-diol, which was used in the next step without further purification.

B. Preparation of a Compound of Formula (4)

Similarly, following the procedure of 3A above, but replacing 4-(6-{[(1R,2R)-2-(phenylmethoxy)cyclopentyl]amino}purin-9-yl)(6S,3aR,6aR)-6-(chloromethyl)-4H,6H, 3aH,6aH-oxolano[3,4-d]1,3,2-dioxathiolan-2-one with other isomers of 4-(6-{[2-(phenylmethoxy)cyclopent amino}purin-9-yl)(6S,3aR,6aR)-6-(chloromethyl)-4H,6H, 3aH,6aH-oxolano[3,4-d]1,3,2-dioxathiolan-2-one, the following compounds are made:

2-(6-{[(1S,2S)-2-(phenylmethoxy)cyclopentyl]amino}purin-9-yl)(4S,5S,3R)-5-(chloromethyl)oxolane-3,4-diol;

2-(6-{[(1R,2S)-2-(phenylmethoxy)cyclopentyl]amino}purin-9-yl)(4S,5S,3R)-5-(chloromethyl)oxolane-3,4-diol;

2-(6-{[(1S,2R)-2-(phenylmethoxy)cyclopentyl]amino}purin-9-yl)(4S,5S,3R)-5-(chloromethyl)oxolane-3,4-diol; and 2-(6-{[(1RS,2RS)-2-(phenylmethoxy)cyclopentyl]amino}purin-9-yl)(4S,5 S,3R)-5-(chloromethyl)oxolane-3,4-diol.

EXAMPLE 4

Preparation of a Compound of Formula (5)

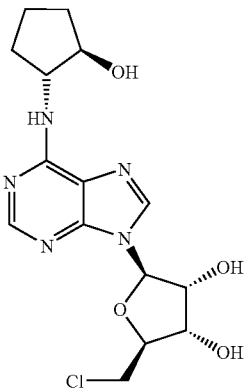

The 2-(6-{[(1R,2R)-2-(phenylmethoxy)cyclopentyl]amino}purin-9-yl)(4S,5S,3R)-5-(chloromethyl)oxolane-3,4-diol obtained in Example 3 (22 g) was dissolved in ethanol (450 mL) and cyclohexane (200 mL). To this solution was added palladium hydroxide (20 mole %, 1 gram added initially, 1 gram after 6 hours, and 1 gram after 14 hours), and the reaction mixture was refluxed for 18 hours. The reaction mixture was filtered thru celite while still hot, and solvent removed from the filtrate under reduced pressure. The product was triturated with ethanol (20 mL), filtered, and washed with ethanol, to afford 2-{6-[((1R,2R)-2-hydroxycyclopentyl)amino]purin-9-yl}(4S,5S,3R)-5-(chloromethyl)oxolane-3,4-diol as a white powder (7.3 grams).

Further material was recovered by suspending the retrieved palladium hydroxide in methanol (200 mL), and warming the mixture at 90° C. for 1 hour. The hot mixture was filtered thru celite, and the celite was further washed with hot methanol. The filtrate was concentrated under reduced pressure, and the residue triturated with ethanol (20 mL) to afford a further 8.6 grams of 2-{6-[((1R,2R)-2-hydroxycyclopentyl)amino]purin-9-yl}(4S,5 S,3R)-5-(chloromethyl)oxolane-3,4-diol.

$^1$H NMR (DMSO-d6) δ 1.64-2.18 (m, 6 H), 3.26-3.29 (m, 1H, NHCH), 3.83-3.97 (m, 2H, CH$_2$Cl 5'), 4.03-4.09 (m, 1H, CH-4'), 4.12-4.17 (m, 1H, CHOH), 4.16-4.19 (m, 1H, 3'CH), 4.84-4.92 (m, 1H, 2'CH), 5.96 (d, J=6 Hz, 1H, H-1'), 7.23-7.35 (m, 5H, PhH), 8.15 (S, 1H, C-2H), 8.39 (s, 1H, C-8H).

B. Preparation of a Compound of Formula (5)

Similarly, following the procedure of 4A above, but replacing 2-(6-{[(1R,2R)-2-(phenylmethoxy)cyclopentyl]amino}purin-9-yl)(4S,5S,3R)-5-(chloromethyl)oxolane-3,4-diol by other isomers of 2-(6-{[2-(phenylmethoxy)cyclopentyl]amino}purin-9-yl)(4S,5S,3R)-5-(chloromethyl)oxolane-3,4-diol, the following compounds are made:

2-(6-{[(1S,2S)-2-(phenylmethoxy)cyclopentyl]amino}purin-9-yl)(4S,5S,3R)-5-(chloromethyl)oxolane-3,4-diol;

2-(6-{[(1R,2S)-2-(phenylmethoxy)cyclopentyl]amino}purin-9-yl)(4S,5S,3R)-5-(chloromethyl)oxolane-3,4-diol;

2-(6-{[(1S,2R)-2-(phenylmethoxy)cyclopentyl]amino}purin-9-yl)(4S,5 S,3R)-5-(chloromethyl)oxolane-3,4-diol; and 2-(6-{[(1RS,2RS)-2-(phenylmethoxy)cyclopentyl]amino}purin-9-yl)(4S,5S,3R)-5-(chloromethyl)oxolane-3,4-diol.

EXAMPLE 5

Preparation of a Compound of Formula I in which R is 2-Fluorophenyl

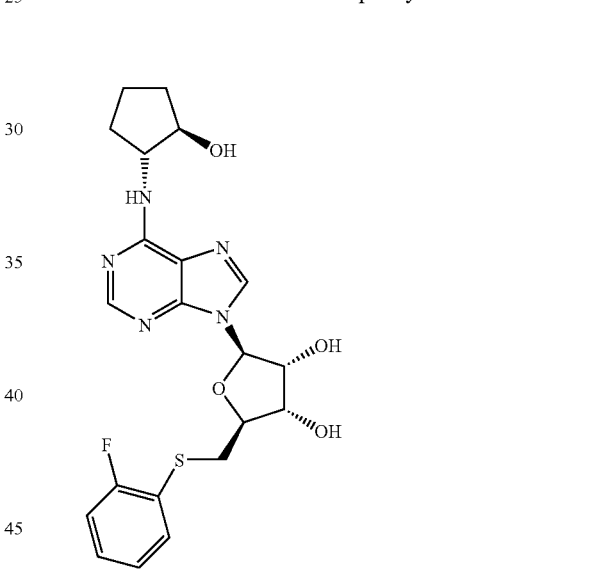

To a solution of 2-fluorothiophenol (38 mL, 406 mmol) in 2N sodium hydroxide (100 mL) was added 2-{6-[((1R,2R)-2-hydroxycyclopentyl)amino]purin-9-yl}(4S,5S,3R)-5-(chloromethyl)oxolane-3,4-diol (15.0 g, 40.6 mmol) in N,N-dimethylformamide (120 mL). The mixture was warmed to 100 C for 4 hours, following the progress of the reaction by TLC. The N,N-dimethylformamide was removed under reduced pressure, and the remaining mixture was diluted with water (200 mL), neutralized with acetic acid, extracted with ethyl acetate (3×125 mL), and the combined organic layers were dried over MgSO$_4$. After removing the solvent under reduced pressure the residue was triturated with diethyl ether and filtered, to afford 16 grams of 2-{6-[((1R,2R)-2-hydroxycyclopentyl)amino]purin-9-yl}(4S,5 S,3R)-5-[(2-fluorophenylthio)methyl]oxolane-3,4-diol as a white powder (85% yield).

$^1$H NMR (DMSO-d6) δ 1.66-2.27 (m, 6 H), 3.42-3.59 (m, 1H, NHCH), 4.05-4.14 (m, 2H), 4.03-4.09 (m, 1H, CH-4'), 4.14-4.19 (m, 1H), 4.16-4.19 (m, 1H, 3'CH), 4.84-4.92 (m, 1H, 2'CH), 5.97 (d, J=6 Hz, 1H, H-1'), 7.05-7.55 (m, 4H, PhH), 8.10 (S, 1H, C-2H), 8.15 (s, 1H, C-8H).

B. Preparation of a Compound of Formula I in which R is 2-Fluorolphenyl

Similarly, following the procedure of 5A above, but replacing 2-{6-[((1R,2R)-2-hydroxycyclopentyl)amino]purin-9-yl}(4S,5S,3R)-5-(chloromethyl)oxolane-3,4-diol by other isomers of 2-{6-[(2-hydroxycyclopentyl)amino]purin-9-yl}(4S,5S,3R)-5-(chloromethyl)oxolane-3,4-diol, the following compounds are made:

2-{6-[((1S,2S)-2-hydroxycyclopentyl)amino]purin-9-yl} (4S,5S,3R)-5-[(2-fluorophenylthio)methyl]oxolane-3,4-diol;

2-{6-[((1R,2S)-2-hydroxycyclopentyl)amino]purin-9-yl} (4S,5S,3R)-5-[(2-fluorophenylthio)methyl]oxolane-3,4-diol;

2-{6-[((1S,2R)-2-hydroxycyclopentyl)amino]purin-9-yl} (4S,5S,3R)-5-[(2-fluorophenylthio)methyl]oxolane-3,4-diol; and 2-{6-[((1RS,2RS)-2-hydroxycyclopentyl)amino]purin-9-yl}(4S,5S,3R)-5-[(2-fluorophenylthio)methyl]oxolane-3,4-diol.

C. Preparation of a Compound of Formula I varying R

Similarly, following the procedure of 5A above, but replacing 2-fluorothiophenol by other thiophenols of formula RSH, other compounds of Formula I are prepared.

EXAMPLE 6

Binding Assays—DDT$_1$ Cells

Cell Culture

DDT cells (hamster vas deferens smooth muscle cell line) were grown as monolayers in petri dishes using Dulbecco's Modified Eagle's Medium (DMEM) containing 2.5 µg ml-1 amphotericin B, 100 U ml-1 penicillin G, 0.1 mg ml-1 streptomycin sulfate and 5% fetal bovine serum in a humidified atmosphere of 95% air and 5% CO$_2$. Cells were subcultured twice weekly by dispersion in Hank's Balanced Salt Solution (HBSS) without the divalent cations and containing 1 mM EDTA. The cells were then seeded in growth medium at a density of 1.2×105 cells per plate and experiments were performed 4 days later at approximately one day preconfluence.

Membrane Preparations

Attached cells were washed twice with HBSS (2×10 ml), scraped free of the plate with the aid of a rubber policeman in 5 ml of 50 mM Tris-HCl buffer pH 7.4 at 4° C. and the suspension homogenized for 10 s. The suspension was then centrifuged at 27,000×g for 10 min. The pellet was resuspended in homogenization buffer by vortexing and centrifuged as described above. The final pellet was resuspended in 1 vol of 50 mM Tris-HCl buffer pH 7.4 containing 5 mM MgCl$_2$ for A$_1$ AdoR assays. For the [$^{35}$S]GTPγS binding assay the final pellet was resuspended in 50 mM Tris-HCl pH 7.4 containing 5 mM MgCl$_2$, 100 mM NaCl and 1 mM dithiothreitol. This membrane suspension was then placed in liquid nitrogen for 10 min, thawed and used for assays. The protein content was determined with a Bradford™ Assay Kit using bovine serum albumin as standard.

Competitive Binding Assay

Pig striatum were prepared by homogenation in 50 mM Tris buffer (5× volume of tissue mass pH=7.4). After centrifugation at 19,000 rpm for 25 minutes at 4° C., the supernatant was discarded, and the process was repeated twice. Compounds of Formula I were assayed to determine their affinity for the A$_1$ receptor in a pig striatum membrane prep or a DDT$_1$ membrane prep. Briefly, 0.2 mg of pig striatal membranes or DDT$_1$ cell membranes were treated with adenosine deaminase and 50 mM Tris buffer (pH=7.4) followed by mixing. To the pig membranes was added 2 µL of serially diluted DMSO stock solution of the compounds of this invention at concentrations ranging from 100 microM to 10 nM. The control received 2 microL of DMSO alone, then the antagonist [$^3$H] 8-cyclopentylxanthine (CPX) for pig striatum or the agonist [$^3$H] 2-chloro-6-cyclopentyladenosine (CCPA) for DDT$_1$ membranes in Tris buffer (50 mM, pH of 7.4) was added to achieve a final concentration of 2 nM. After incubation at 23 C for 2 h, then the solutions were filtered using a membrane harvester using multiple washing of the membranes (3×). The filter disks were counted in scintillation cocktail affording the amount of displacement of tritiated CPX or by the competitive binding of compounds of Formula I.

The compounds of Formula I are shown to be of high, medium, or low affinity for the A$_1$ adenosine receptor in this assay.

EXAMPLE 7

[$^{35}$S]GTPγS Binding Assays

A$_1$-agonist stimulated [$^{35}$S] GTPγS binding was determined by a modification of the method described by Giersckik et al. (1991) and Lorenzen et al. (1993). Membrane protein (30-50 µg) was incubated in a volume of 0.1 ml containing 50 mM Tris-HCl buffer pH 7.4, 5 mM MgCl$_2$, 100 mM NaCl, 1 mM dithiothreitol, 0.2 units ml$^{-1}$ adenosine deaminase, 0.5% BSA, 1 mM EDTA, 10 mM GDP, 0.3 nM [35S]GTPγS and with or without varying concentrations of CPA for 90 min at 30° C. Nonspecific binding was determined by the addition of 10 µM GTPγS. Agonist stimulated binding was determined as the difference between total binding in the presence of CPA and basal binding determined in the absence of CPA. Previous reports have shown that agonist stimulated [$^{35}$S]GTPγS binding was dependent on the presence of GDP (Gierschik et al., 1991; Lorenzen et al., 1993; Traynor & Nahorski, 1995). In preliminary experiments, it was found that 10 µM GDP gave the optimal stimulation of CPA dependent [$^{35}$S]GTPγS binding and this concentration was therefore used in all studies. In saturation experiments, 0.5 nM [$^{35}$S]GTPγS was incubated with 0.5-1000 nM GTPγS. At the end of the incubation, each suspension was filtered and the retained radioactivity determined as described above.

The compounds of Formula I are shown to be partial or full agonists of the A$_1$ adenosine receptor in this assay.

EXAMPLE 8 cAMP Assay

A scintillation proximity assay (SPA) using rabbit antibodies directed at cAMP using an added tracer of adenosine 3',5'-cyclic phosphoric acid 2'-O-succinyl-3-[$^{125}$I]iodotyrosine methyl ester and fluoromicrospheres containing anti-rabbit specific antibodies as described by Amersham Pharmacia Biotech (Biotrak cellular communication assays). Briefly, DDT$_1$ cells were cultured in clear bottomed 96 well microtiter plates with opaque wells at concentrations between 10$^4$ to 10$^6$ cells per well in 40 µl of HBSS at 37° C.

(5% CO$_2$ and 95% humidity). The partial or full A$_1$ agonists (5 µl) of this invention were incubated at various concentrations with the DDT$_1$ cells in the presence of rolipram (50 µM), and 5 µM forskolin for 10 min at 37° C. The cells were immediately lysed by treatment 5 µl of 10% dodecyltrimethylammonium bromide followed by shaking using microplate shaker. After incubation of the plate for 5 minutes, an immunoreagent solution (150 µl containing equal volumes of tracer, antiserum, and SPA fluorospheres) was added to each well followed by sealing the plate. After 15-20 h at 23° C., the amount of bound [$^{125}$I] cAMP to the fluoromicrospheres was determined by counting in a microtitre plate scintillation counter for 2 minutes. Comparison of counts with standard curves generated for cAMP using a similar protocol afforded the cAMP present after cell lysis.

The compounds of Formula I are shown to be functionally active as A$_1$ agonists with a partial or full decrease in cAMP in this assay.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed is:
1. A method of preparing compounds of Formula I:

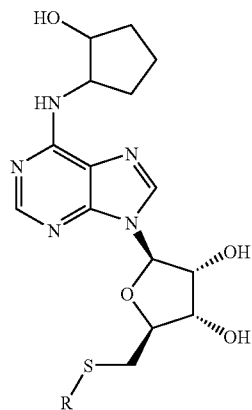

Formula I wherein R is optionally substituted phenyl,
comprising the steps of:
  a. in the presence of base, contacting (4S,2R,3R,5R)-2-(6-chloropurin-9-yl)-5-(hydroxymethyl)oxolane-3,4-diol with a protected (2-hydroxy) cyclopentylamine compound having a protecting group on the 2-hydroxy moiety;
  b. contacting the product of step (a) with thionyl chloride in the presence of a second base;
  c. contacting the product of step (b) with a third base;
  d. removing the protecting group from the 2-hydroxy moiety either before or after reacting the product of step (c) with a compound of the formula RSH in the presence of a fourth base.

2. The method of claim 1, wherein the protecting group is removed from the 2-hydroxy moiety before the reaction of the product of step (c) with the compound of formula RSH.

3. The method of claim 2, wherein the protecting group is a phenylmethoxy group.

4. The method of claim 3, wherein the protecting group is removed by reaction of the product of step (c) with a partially unsaturated cycloalkyl compound or ammonium formate in the presence of a catalyst.

5. The method of claim 4, wherein the protecting group is removed by reaction of the product of step (c) with a partially unsaturated cycloalkyl compound.

6. The method of claim 5, wherein the partially unsaturated cycloalkyl compound is cyclohexene.

7. The method of claim 4, wherein the protecting group is removed by reaction of the product of step (c) with ammonium formate in the presence of a catalyst.

8. The method of claim 4, wherein the catalyst is palladium hydroxide.

9. The method of claim 4, wherein the protecting group is removed in a protic solvent.

10. The method of claim 9, wherein the protic solvent is ethanol.

11. The method of claim 2, wherein the protecting group is removed from the 2-hydroxy moiety after the reaction of the product of step (c) with the compound of formula RSH.

12. The method of claim 11, wherein the protecting group is a t-butyldimethylsilyl group and it is removed by reaction with NH$_4$F in methanol.

13. The method of claim 1, wherein the reaction with the compound of the formula RSH in step (d) is carried out in the presence of an excess of sodium hydroxide.

14. The method of claim 1, wherein the reaction with the compound of the formula RSH in step (d) is carried out in a polar solvent.

15. The method of claim 14, wherein the polar solvent is N,N-dimethylformamide.

16. The method of claim 1, wherein R is 2-fluorophenyl.

17. The method of claim 1, wherein the 6-substituent on the Formula I compound is (1R,2R)-2-hydroxycyclopentyl) amino.

18. The method of claim 1, wherein step (a) is carried out in the presence of an inert solvent.

19. The method of claim 18, wherein the inert solvent is ethanol.

20. The method of claim 1, wherein the base used in step (a) is triethylamine.

21. The method of claim 1, wherein the second base used in step (b) is pyridine.

22. The method of claim 1, wherein step (b) is carried out in an inert solvent.

23. The method of claim 22, wherein the inert solvent is acetonitrile.

24. The method of claim 1, wherein the third base used in step (c) is ammonia.

25. The method of claim 1, wherein step (c) is carried out in the presence of a protic solvent.

26. The method of claim 25, wherein the protic solvent is methanol.

27. A method of preparing a compound of the formula (5):

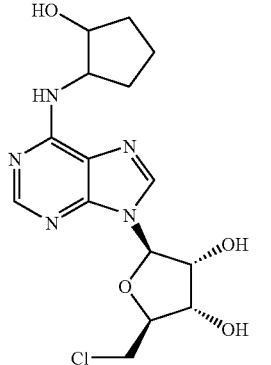
(5)

comprising contacting a compound of the formula (4):

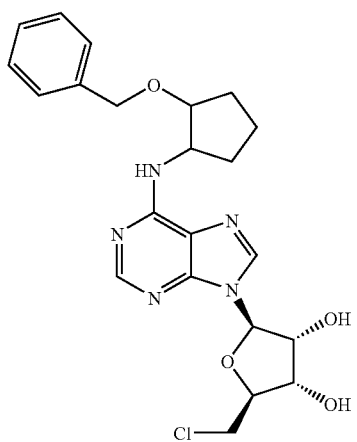
(4)

with a partially unsaturated cycloalkyl compound in the presence of a catalyst.

28. A method of preparing a compound of the formula (4):

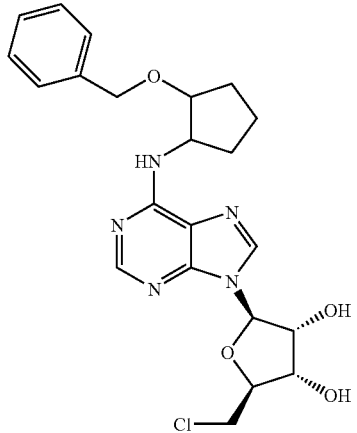
(4)

comprising contacting a compound of formula (3):

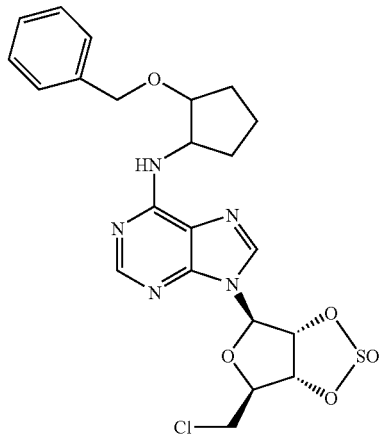
(3)

with a base.

29. A method of preparing a compound of formula (3):

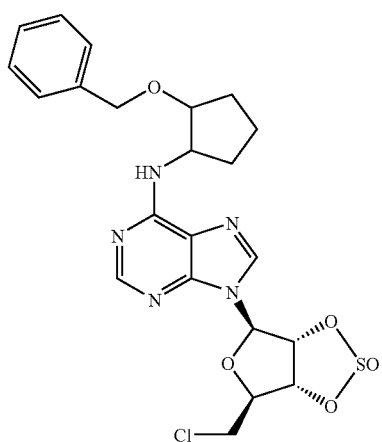
(3)

comprising contacting a compound of the formula (2):

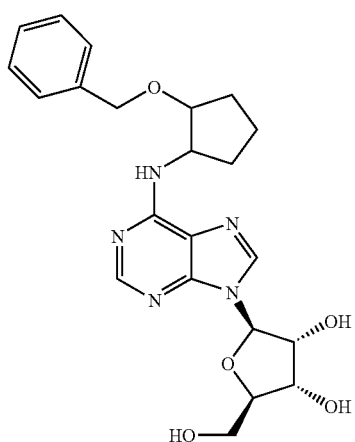
(2)

with thionyl chloride in the presence of a base.

* * * * *